(12) United States Patent
Hoshino et al.

(10) Patent No.: US 8,343,544 B2
(45) Date of Patent: Jan. 1, 2013

(54) ORAL SUSTAINED-RELEASE TABLET

(75) Inventors: Ryouichi Hoshino, Tochigi (JP);
Katashi Nakashima, Tatebayashi (JP);
Kazuo Kazama, Tochigi (JP)

(73) Assignees: Kyorin Pharmaceutical Co., Ltd.,
Tokyo (JP); Ono Pharmaceutical Co., Ltd., Osaka (JP)

( * ) Notice: Subject to any disclaimer, the term of this patent is extended or adjusted under 35 U.S.C. 154(b) by 67 days.

(21) Appl. No.: 12/855,226

(22) Filed: Aug. 12, 2010

(65) Prior Publication Data

US 2010/0305179 A1 Dec. 2, 2010

Related U.S. Application Data

(63) Continuation of application No. 10/566,503, filed as application No. PCT/JP2004/011067 on Aug. 3, 2004, now abandoned.

(30) Foreign Application Priority Data

Aug. 4, 2003 (JP) ................................ 2003-286096

(51) Int. Cl.
*A61K 9/22* (2006.01)
(52) U.S. Cl. ....................................................... 424/468
(58) Field of Classification Search ........................ None
See application file for complete search history.

(56) References Cited

U.S. PATENT DOCUMENTS

| | | | |
|---|---|---|---|
| 4,734,285 A | 3/1988 | Alderman | |
| 4,803,079 A | 2/1989 | Hsiao et al. | |
| 5,334,392 A | 8/1994 | Cuine et al. | |
| 5,399,359 A | 3/1995 | Baichwal | |
| 7,351,429 B1 * | 4/2008 | Ohyama et al. | 424/465 |
| 2004/0024018 A1 | 2/2004 | Kanikanti et al. | |

FOREIGN PATENT DOCUMENTS

| | | |
|---|---|---|
| EP | 1245232 | 10/2002 |
| JP | 62-048618 | 3/1987 |
| JP | 07-215943 | 8/1995 |
| JP | 10-67657 | 3/1998 |
| JP | 2001-172181 | 6/2001 |
| WO | 01/34147 | 5/2001 |
| WO | WO 0134147 A1 * | 5/2001 |
| WO | 01/76557 | 10/2001 |
| WO | 02/00219 | 1/2002 |

OTHER PUBLICATIONS

Publication of South African Application No. 20007548, filed Dec. 15, 2000.
International Search Report issued Nov. 22, 2004 in International (PCT) Application No. PCT/JP2004/011067.
Supplementary European Search Report issued Oct. 23, 2008 in corresponding European Application No. 04748200.

(Continued)

*Primary Examiner* — Nissa Westerberg
(74) *Attorney, Agent, or Firm* — Wenderoth, Lind & Ponack, L.L.P.

(57) ABSTRACT

(Object) An oral sustained-release tablet is provided, which does not cause initial rapid increases in the bloodlevels of 4-(2-methyl-1-imidazolyl)-2,2-diphenylbutylamide (KRP-197) and can maintain constant the blood levels.

(Solving means) An oral sustained-release tablet comprises a pharmaceutical composition and a gel-forming material, the pharmaceutical composition containing KRP-197 as an active ingredient.

6 Claims, 1 Drawing Sheet

OTHER PUBLICATIONS

Hiroyuki Miyachi et al., "Synthesis and Antimuscarinic Activity of a Series of 4-(1-Imidazolyl)-2, 2-diphenylbutyramides: Discovery of Potent and Subtype-selective Antimuscarinic Agents", Bioorganic & Medicinal Chemistry, 7, pp. 1151-1161, 1999.

Gerhartz et al., Ullmann's Encyclopedia of Industrial Chemistry, 1988, XP-002498421, pp. 7-21 to 7-23.

Garely et al., "Current pharmacotherapeutic strategies for overactive bladder", 2002, XP-001097208, pp. 827-833.

\* cited by examiner

ORAL SUSTAINED-RELEASE TABLET

This application is a continuation of U.S. application Ser. No. 10/566,503, filed Feb. 6, 2006, now abandoned, which is a national stage application of International Application No. PCT/JP2004/011067, filed Aug. 3, 2004.

TECHNICAL FIELD

The present invention relates to oral sustained-release tablets that can maintain constant blood levels of 4-(2-methyl-1-imidazolyl)-2,2-diphenylbutylamide (which is referred to as KRP-197, hereinafter), a candidate compound for the treatment for increased urinary frequency and urinary incontinence.

BACKGROUND ART

Urinary incontinence of elderly people has become a public concern and increasing efforts have been devoted to the development of treatment for increased urinary frequency and urinary incontinence. KRP-197, a novel compound developed by Kyorin Pharmaceutical Co., Ltd. (Patent Document 1), is a selective muscarinic antagonist and is considered as a medicinal candidate compound for the treatment for increased urinary frequency and urinary incontinence (Non-Patent Document 1). An oral solid preparation has already been described as a type of KRP-197 preparation, (Patent Document 2).

Although KRP-197 is rapidly absorbed after an oral administration, the drug has a relatively short half-life and needs to be administered several times a day when given in the form of conventional oral solid preparation.
[Patent Document 1] Japanese Patent Laid-Open Publication No. Hei 7-15943
[Patent Document 2] WO 01/34147 A1 pamphlet
[Non-Patent Document 1] Bioorg. Med. Chem., 1999, 7, 1151-1161.

DISCLOSURE OF THE INVENTION

Problems to be Solved by the Invention

Urinary frequency and urinary incontinence strip sufferers of freedom of leaving their home for a long time. Thus, a medication that can be taken less frequently not only improves the quality of patients' lives, but also ensures proper use of the drug by decreasing in the chance of patients forgetting to take medication. In addition, muscarinic antagonists are known to cause thirst as the side effect. Therefore, avoiding rapid increases in the blood levels of these compounds should prevent this side effect. The present invention is thus intended to provide an oral sustained-release tablet of KRP-197 that does not cause initial rapid increases in the KRP-197 blood levels and can maintain the constant blood levels.

Means for Solving the Problems

The preset inventors in their attempt have formulated a pharmaceutical composition containing KRP-197 and a gel-forming material and compressed into tablets. The resulting oral tablets are capable of sustained release of KRP-197.

Accordingly, the present invention concerns the following oral sustained-release tablets:

1) An oral sustained-release tablet comprising a pharmaceutical composition and a gel-forming material, the pharmaceutical composition containing KRP-197 as an active ingredient;
2) The oral sustained-release tablet according to 1), wherein the gel-forming material is hydroxypropylmethylcellulose;
3) The oral sustained-release tablet according to 1), wherein the pharmaceutical composition contains 18 to 73 wt % of hydroxypropylmethylcellulose;
4) The oral sustained-release tablet according to 1), obtained by mixing KRP-197-containing granules with a composition containing a gel-forming material; and
5) The oral sustained-release tablet according to 4), wherein KRP-197-containing granules are manufactured by using a solution of KRP-197.

Advantage of the Invention

The oral sustained-release tablets swell as the gel-forming material absorbs water and the resulting gel layer controls the diffusion of the drug from the tablets.

BEST MODE FOR CARRYING OUT THE INVENTION

Figure 1:
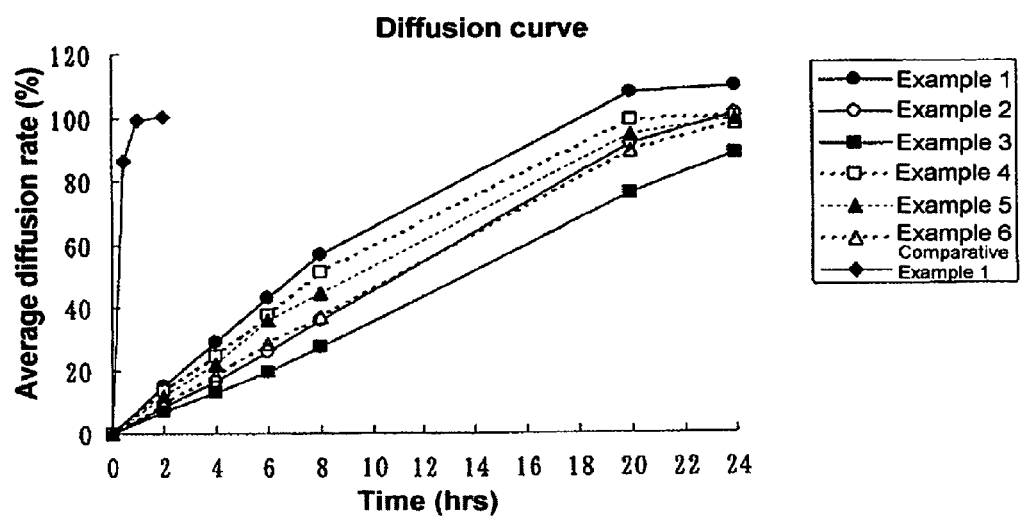
FIG. 1 shows the dissolution curves for Examples 1 through 6 and Comparative Example 1.

KRP-197, the active ingredient of the oral sustained-release tablets in the present invention, is 4-(2-methyl-1-imidazolyl)-2,2-diphenylbutylamide, a bladder-selective choline antagonist effective in the treatment for increased urinary frequency and urinary incontinence.

The gel-forming material using for the oral sustained-release tablets in the present invention is a material that swells as it absorbs a solvent, so that the colloid particles in the material are cross-linked between polymers to form a three-dimensional network structure, resulting in a less-fluid gel-like material. When used in pharmaceutical preparations, the material serves mainly as a binder, thickener viscosity increasing-agent and sustained-release agent. Examples of the gel-forming material include gum Arabic, agar, polyvinylpyrrolidone, sodium alginate, alginic acid propyleneglycol ester, carboxyvinyl polymer, carboxymethylcellulose, sodium carboxymethylcellulose, guar gum, gelatin, hydroxypropylmethylcellulose, hydroxypropylcellulose, polyvinylalcohol, methylcellulose, and hydroxyethylmethylcellulose. Of these, hydroxypropylcellulose (referred to as HPMC, hereinafter) is particularly preferred and provides one feature of the present invention.

HPMC is commercially available from Shin-Etsu Chemical Co., Ltd. under the trade name of "metlose." Many different types of the product are available with varying degrees of substitution by hydroxypropoxyl or methoxyl groups and varying viscosities. Metlose 60SH (HPMC2910) and Metlose 90SH (HPMC2208) with an average viscosity of 4000 cps are particularly suitable for use in the present invention.

The amount of the gel-forming material, such as HPMC, used in the KRP-197-containing pharmaceutical composition is preferably 18 to 73 wt %.

Aside from the gel-forming material, the pharmaceutical composition may contain other components commonly used in the production of pharmaceutical products, including excipients (including sugars such as lactose and glucose, sugar alcohols such as D-sorbitol and mannitol, celluloses such as crystalline cellulose, and starches such as corn starch and partly pregelatinized starch, with partly pregelatinized starch particularly preferred), lubricants (such as magnesium stearate, calcium stearate, talc, and hardened oil, with magnesium stearate particularly preferred) and higher alcohols (such as lauryl alcohol, cetanol, stearyl alcohol, oleyl alcohol, and lanolin alcohol). If necessary, a binder or a pH adjustor may be added (for example, organic acids such as adipic acid, ascorbic acid, erythorbic acid, citric acid, gluconic acid, succinic acid, tartaric acid, fumaric acid, malic acid, aspartic acid, glutamic acid, and alginic acid).

The oral sustained-release tablets in the present invention can be produced by adding a powder of the gel-forming material, such as HPMC, to the KRP-197-containing pharmaceutical composition, and directly compressing the material into tablets. Alternatively, the material comprising the gel-forming material and the KRP-containing pharmaceutical composition may first be formed into granules by a common technique, so that the granules can be compressed into tablets.

It is preferred to first prepare a granular composition by mixing the KRP-197-containing granules with a gel-forming material, and then compressing the granular composition into tablets.

In preparing the KRP-197-containing granules, KRP-197 is preferably added in the form of a solution. This allows production of more uniform granules and ensures that the granules contain uniform amounts of KRP-197. While the solvent to make the solution may be any solvent that can dissolve KRP-197, it is preferably a mixture of ethanol and water, in particular, a mixture composed of 100 parts by weight of ethanol and 20 to 40 parts by weight of water.

When desired, the tablets may be coated with film by a common technique. While the coat may be any material, aqueous polymers commonly used for this purpose are preferred.

The oral sustained-release tablets produced in accordance with the present invention may contain relatively small amounts of the active ingredient. Specifically, the pharmaceutical composition used in a single dose of the tablets may contain KRP-197 in an amount of 0.025 to 5 mg, preferably in an amount of 0.1 to 1 mg, and more preferably in an amount of 0.2 to 0.7 mg.

The present invention will now be described in detail with reference to examples, which are not intended to limit the scope of the present invention in any way.

EXAMPLE 1

710 g of a partly pregelatinized starch (Trade name "Starch 1500G," Colorcon Co., Ltd.) was placed in a flow coater FBG-5 (Freund Co., Ltd.). KRP-197 was dissolved in a mixture of ethanol (95), and water (ethanol (95): water: KRP-197=76.1:22.5:1.4 (by wt %)) and 1250 g of this solution was sprayed to give a granular product, which was then sieved through a 850 μm sieve to obtain uniform KRP-197-containing granules. To 14.55 g of the KRP-197-containing granules, 30 g of partly pregelatinized starch, 10 g of hydroxypropylmethylcellulose 2910 (Trade name "Metlose 60SH-4000," Shin-Etsu Chemical Co., Ltd.), and 0.45 g of magnesium stearate (Taihei Chemical Industrial Co., Ltd.) were added, and the components were mixed together to give granules for making tablets. Using a single punch tablet machine (Okada Seiko Co., Ltd.), the granules were compressed into tablets with a diameter of 6.5 mm and a weight of 110 mg (KRP-197 content in one tablet ~0.7 mg).

EXAMPLE 2

710 g of a partly pregelatinized starch was placed in a flow coater FBG-5. KRP-197 was dissolved in a mixture of ethanol (95) and water (ethanol (95): water: KRP-197=76.1:22.5:1.4 (by wt %)), and 1250 g of this solution was sprayed to give a granular product, which was then sieved through an 850 μm sieve to obtain uniform KRP-197-containing granules. To 14.55 g of the KRP-197-containing granules, 4 0 g of hydroxypropylmethylcellulose 2910, and 0.45 g of magnesium stearate were added, and the components were mixed together to give granules for making tablets. Using a single punch tablet machine, the granules were compressed into tablets with a diameter of 6.5 mm and a weight of 110 mg (KRP-197 content in one tablet=0.7 mg).

EXAMPLE 3

710.0 g of a partly pregelatinized starch was placed in a flow coater FBG-5. KRP-197 was dissolved in a mixture of ethanol (95) and water (ethanol (95): water: KRP-197=76.1:22.5:1.4 (by wt %)), and 1250 g of this solution was sprayed to give a granular product, which was then sieved through an 850 μm sieve to obtain uniform KRP-197-containing granules. To 14.55 g of the KRP-197-containing granules, 14.55 g of partly pregelatinized starch, 80 g of hydroxypropylmethylcellulose 2910, and 0.9 g magnesium stearate were added, and the components were mixed together to give granules for making tablets. Using a single punch tablet machine, the granules were compressed into tablets with a diameter of 8 mm and a weight of 220 mg (KRP-197 content in one tablet=0.7 mg).

EXAMPLE 4

3262.5 g of a partly pregelatinized starch was placed in a flow coater FBG-5. KRP-197 was dissolved in a mixture of ethanol (95) and water (ethanol (95): water: KRP-197=76.1:22.5:1.4 (by wt %)), and 2678.6 g of this solution was sprayed to give a granular product, which was then sieved through an 850 μm sieve to obtain uniform KRP-197-containing granules. To 396 g of the KRP-197-containing granules, 724.5 g of partly pregelatinized starch, 360 g of hydroxypropylmethylcellulose 2910, and 4.5 g of magnesium stearate were added, and the components were mixed together to give granules for making tablets. Using rotary tabletting machine (Hata Iron Works Co., Ltd.), the granules were compressed into tablets with a diameter of 7.5 mm and a weight of 165 mg (KRP-197 content in one tablet=0.5 mg).

EXAMPLE 5

1087.5 g of a partly pregelatinized starch was placed in a flow coater FBG-5. KRP-197 was dissolved in a mixture of ethanol (95) and water (ethanol (95): water: KRP-197-76.1:22.5:1.4 (by wt %)), and 894 g of this solution was sprayed to give a granular product, which was then sieved through an 850 μm sieve to obtain uniform KRP-197-containing granules. To 352 g of the KRP-197-containing granules, 320 g of partly pregelatinized starch, 640 g of hydroxypropylmethylcellulose 2910, and 8.0 g magnesium stearate were added, and the components were mixed together to give granules for making tablets. Using a rotary tabletting machine, the granules were compressed into tablets with a diameter of 7.5 mm and a weight of 165 mg (KRP-197 content in one tablet=0.5 mg).

EXAMPLE 6

1087.5 g of a partly pregelatinized starch was placed in a flow coater FBG-5. KRP-197 was dissolved in a mixture of ethanol (95) and water (ethanol (95): water: KRP-197=76.1:22.5:1.4 (by wt %)), and 894 g of this solution was sprayed to give a granular product, which was then sieved through an 850 μm sieve to obtain uniform KRP-197-containing granules. To 352 g of the KRP-197-containing granules, 960 g of hydroxypropylmethylcellulose 2910, and 8.0 g of magnesium stearate were added, and the components were mixed together to give granules for making tablets. Using a rotary tabletting machine, the granules were compressed into tablets with a diameter of 7.5 mm and a weight of 165 mg (KRP-197 content in one tablet=0.5 mg).

Comparative Example 1

243.2 g of a partly pregelatinized starch and 970.8 g of crystalline cellulose (Trade name "Abicel PH-301," Asahi Kasei Co., Ltd.) were placed in a flow coater FBG-5.2 g of KRP-197 and 12.8 g of polyvinylpyrrolidone (Trade name "Povidone," BASF Co., Ltd.) were dissolved in an ethanol (95)/water mixture (1:1 (by wt %)), and the solution was sprayed to give a granular product, which was then sieved through a 850 μm sieve to obtain uniform KRP-197-containing granules. To the resulting granules, 3.2 g of magnesium stearate was added and the components were mixed together to obtain granules for making tablets. Using a rotary tabletting machine HT-P18SSII (Hata Iron Works Co., Ltd.), the granules were compressed into simple tablets with a diameter of 7.5 mm and a weight of 154 mg. The resulting tablets were coated with OPADRY 03A45009 (Colorcon) (6 mg per tablet), and a small amount of carnauba wax (Trade name "Polishing wax 103," Freund Co., Ltd.) was added to make film-coated tablets (KRP-197 content in one tablet=0.25 mg).

Experiment Example 1

According to the method 2 of the dissolution test described in Japanese Pharmacopoeia Fourteenth Edition, the tablets of Examples 1 through 6 and Comparative Example 1 were each tested in 900 mL of purified water at 37° C. under the paddle speed of 50 rpm. The results are shown in FIG. 1.

FIG. 1 shows that as opposed to the tablets of Comparative Example 1, each of the tablets in Examples 1 through 6 showed sustained drug release properties.

Experiment Example 2

A tablet of Example 3 or Comparative Example 1 was orally administered to a dog. The time course of KRP-197 concentration in blood is shown in FIG. 2.

Figure 2:
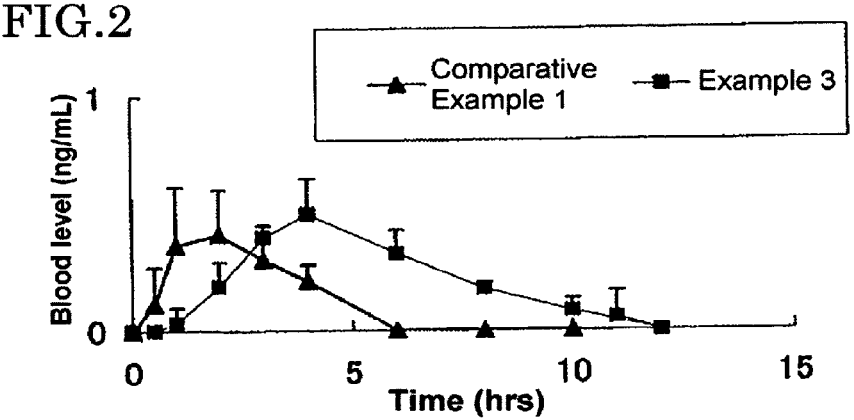
FIG. 2 shows KRP-197 blood levels of Example 3 and Comparative Example 1 in dogs

FIG. 2 shows that in contrast to the KRP-197 blood level observed for the preparation of Comparative Example 1, the KRP-197 bloodlevel increased at a slower rate and showed constant in the tablet of Example 3.

INDUSTRIAL APPLICABILITY

As set forth, the oral sustained-release tablets in the present invention, formed of a pharmaceutical composition containing KRP-197 along with a gel-forming material, shows controlled release of KRP-197. By increasing in the amount of the gel-forming material and the tablet weight, the release of KRP-197 from the oral sustained-release tablets can be extended. Thus, the tablets in the present invention are suitable for use as oral preparations that are intended to be taken once a day.

The invention claimed is:

1. A method of producing an oral sustained-release tablet, said method comprising:
    spraying a solution comprising 4-(2-methyl-1-imidazolyl)-2,2-diphenylbutylamide on to partly pregelatinized starch in a fluidised state to prepare granules comprising 4-(2-methyl-1-imidazolyl)-2,2-diphenylbutylamide;
    mixing the granules with hydroxypropylmethylcellulose in a powder state to prepare a granular composition; and
    compressing the granular composition to form the tablet,
    wherein the tablet comprises 0.2-0.7 mg of 4-(2-methyl-1-imidazolyl)-2,2-diphenylbutylamide.

2. The method according to claim 1, further comprising dissolving the 4-(2-methyl-1-imidazolyl)-2,2-diphenylbutylamide in a solvent of ethanol and water to prepare the solution.

3. The method according to claim 1, wherein the tablet comprises 18 to 73 wt % of the hydroxypropylmethylcellulose.

4. The method according to claim 1, further comprising mixing a partly pregelatinized starch and a lubricant together with the granules and the hydroxypropylmethylcellulose.

5. The method according to claim 4, wherein the lubricant is magnesium stearate.

6. A method of producing an oral sustained-release tablet, said method comprising:
    spraying a solution comprising 4-(2-methyl-1-imidazolyl)-2,2-diphenylbutylamide on to partly pregelatinized starch in fluidized state to prepare granules comprising 4-(2-methyl-1-imidazolyl)-2,2-diphenylbutylamide;
    mixing the granules with hydroxypropylmethylcellulose in a powder state to prepare a granular composition; and
    compressing the granular composition to form a tablet,
    wherein the tablet comprises 18 to 73 wt % of the hydroxypropylmethylcellulose.

* * * * *